(12) United States Patent
Pittaro et al.

(10) Patent No.: US 6,222,860 B1
(45) Date of Patent: Apr. 24, 2001

(54) LASER SYSTEM TOLERATING DISTURBANCES USING MULTIPLE MODES

(75) Inventors: Richard J. Pittaro, San Carlos; David A. King, Menlo Park, both of CA (US); Martin Wunderling, Herrenberg; Jens-Peter Seher, Stuttgart, both of (DE)

(73) Assignee: Hewlett-Packard Company, Palo Alto, CA (US)

(*) Notice: Subject to any disclaimer, the term of this patent is extended or adjusted under 35 U.S.C. 154(b) by 0 days.

(21) Appl. No.: 09/227,105

(22) Filed: Jan. 7, 1999

(51) Int. Cl.[7] .................................................. H01S 3/131
(52) U.S. Cl. ............................ 372/19; 372/9; 372/29.02
(58) Field of Search .................................... 372/9, 18–20, 372/29, 32, 33, 38

(56) References Cited

U.S. PATENT DOCUMENTS

| | | | |
|---|---|---|---|
| 4,622,672 | * 11/1986 | Coldren et al. | 372/32 |
| 4,972,424 | 11/1990 | Wissman | 372/32 |
| 5,065,401 | 11/1991 | Scifres et al. | 372/38 |
| 5,153,671 | 10/1992 | Miles | 356/301 |
| 5,245,405 | 9/1993 | Mitchell et al. | 356/301 |
| 5,432,610 | 7/1995 | King et al. | 356/432 |
| 5,511,087 | 4/1996 | Sato et al. | 372/38 |
| 5,642,375 | 6/1997 | King et al. | 372/97 |
| 5,684,623 | 11/1997 | King et al. | 359/346 |
| 5,914,972 | * 6/1999 | Siala et al. | 372/33 |
| 6,058,128 | * 5/2000 | Ventrudo | 372/33 X |

FOREIGN PATENT DOCUMENTS

WO 96/00997   6/1995   (WO).

OTHER PUBLICATIONS

European Search Report, EP 99 11 7083, Jan. 21, 2000.

* cited by examiner

Primary Examiner—John D. Lee (57) ABSTRACT

A laser system includes a gain medium for providing and amplifying a laser beam within an optical resonator. According to the invention, the laser system actively provides a plurality of different optical modes for stabilizing the laser beam, preferably by forcing the laser beam to jump between different optical modes more frequent than environmental disturbances occur. Providing the plurality of different optical modes can be achieved e.g. by varying the phase of the laser beam and/or by varying the optical length of the optical resonator. The laser system can be employed in a gas monitoring system, e.g. for monitoring a respiration and/or anaesthetic gas, for providing a Raman spectrum of the gas to be monitored.

20 Claims, 6 Drawing Sheets

LASER SYSTEM TOLERATING DISTURBANCES USING MULTIPLE MODES

BACKGROUND OF THE INVENTION

The present invention relates to a laser system comprising a gain medium for providing and amplifying a laser beam within an optical resonator.

Molecules, and in particular gas molecules, are mainly investigated by spectroscopy. Two different spectroscopic methods, i.e. infrared absorption and Raman scattering, are generally applied for airway gas monitoring. The most common and widely spread measuring type is the infrared absorption, since it provides a robust and simple system with reliable accuracy. Disadvantageous, however, is that the infrared absorption is not flexible for upgrading to other molecules. Raman scattering overcomes that disadvantage because each molecule provides its own characteristic scattering signal. In addition and in contrast to the infrared absorption, the wavelength of the excitation light can be chosen flexibly. The drawback of the Raman scattering, however, lies in its minor effect, meaning that an excitation power of a light beam will create only a very low Raman signal (e.g. an excitation power of 1 W will create a Raman signal of 1 pW).

For medical purposes, such as respiratory or anesthetic gas monitoring, Raman scattering has been investigated as shown e.g. by Van Wagenen et al in "Gas Analysis by Raman scattering", Journal of Clinical Monitoring, vol. 2 No. 4, October 1986.

Because of the minor effect in Raman scattering, the optical output power of the excitation light should be selected as high as possible. In addition, to achieve a good resolution of the molecule spectra, the excitation light source should be a narrow band source with a good wavelength and power stability. Thus, laser sources are commonly used as excitation light sources, whereby for reasons of compactness, lifetime and price, semiconductor lasers are normally superior to solid state or gas lasers. However, semiconductor lasers exhibit, in contrast to solid state and gas lasers, the disadvantage of a low internal circulating optical power and a low coupled out optical power.

Figure 1A:
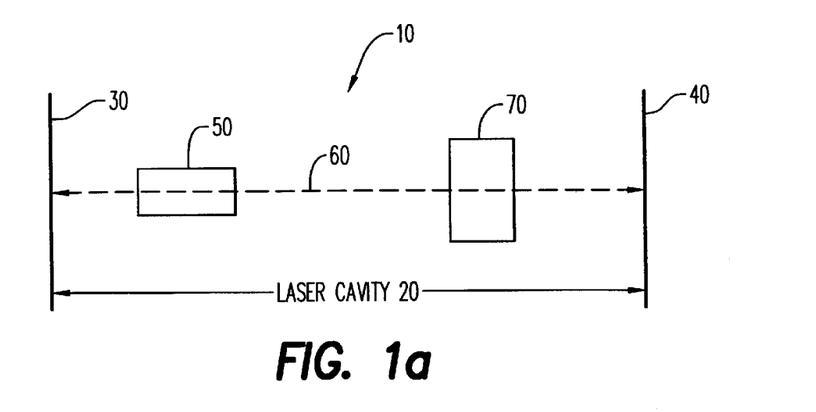
FIGS. 1A and 1B show laser system in the gas analyzing system as known in the art.

A known solution for increasing excitation power for Raman scattering is disclosed in U.S. Pat. No. 5,153,671 and U.S. Pat. No. 5,245,405 for a gas analyzing system. A gas analysis cell employing Raman scattering is positioned within a single optically resonant cavity. The gas flow is directed into the cavity and analyzed within the gas analysis cell. FIG. 1A shows in principle such a laser system 10 in the gas analyzing system of U.S. Pat. No. 5,153,671. The laser system 10 comprises a laser cavity 20 between a first mirror 30 and a second mirror 40. A gain medium 50 provides and amplifies a laser beam 60 which serves as an excitation beam in a gas analysis cell 70 within the laser cavity 20. The first mirror 30 may also be part of the gain medium 50.

Figure 1B:
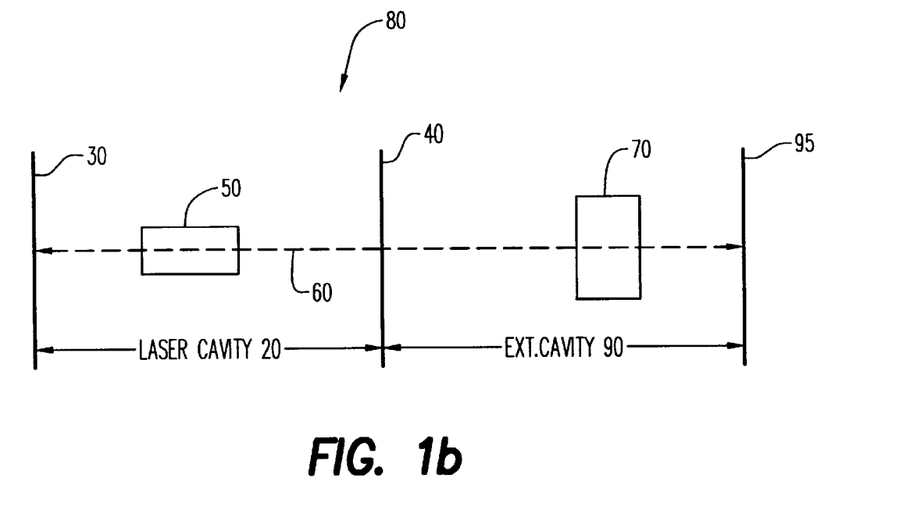

In a more sophisticated solution for increasing excitation power, in particular when semiconductor lasers are used as excitation sources for Raman scattering, the optical output power of the excitation laser is coupled into an external resonator as shown e.g. in U.S. Pat. No. 5,642,375 or U.S. Pat. No. 5,684,623 by the same applicant. FIG. 1B shows in principle such a coupled laser system 80. The coupled laser system 80 comprises the laser cavity 20 between the first mirror 30 and the second mirror 40 and the gain medium 50 providing and amplifying the laser beam 60. An external cavity 90 is provided between the second mirror 40 and a third mirror 95, and is optically coupled to the laser cavity 20. The laser beam 60 serves as excitation beam in the gas analysis cell 70 within the external cavity 90. By applying low loss mirrors with different reflection coefficients for the mirrors 30, 40 and 95, as described e.g. in U.S. Pat. No. 5,642,375, a very high built-up optical power inside the resonator of the external cavity 90 can be achieved. For example, a 10 mW semiconductor laser beam 60 is capable of pumping the external cavity 90 up to several hundreds of Watts. U.S. Pat. No. 5,432,610 further discloses a passive, purely optical locking of a laser diode on an external resonator.

Using such an external pumped resonator, as depicted as the laser system 80 in FIG. 1B, for probing an unknown gas sample in the external cavity 90 will in particular provide enough optical power to excite a Raman signal well above the sensitivity limit of optical sensors. Optical sensors can simply be photodiodes, charged coupled devices or other image sensors for more sophisticated applications.

As well in the single cavity laser system 10 as in the coupled cavity laser system 80, the gas analysis cell 70 represents the principal possibility of probing a gas sample, whereby the gas sample can be analyzed in a specific (separated) environment or directly in the respective cavity. Probing the gas sample can either be accomplished 'offline', i.e. the gas sample is taken and analyzed later (e.g. in a defined environment), or 'online', i.e. the gas sample is directly provided to the gas analysis cell 70 and analyzed. The latter case, in particular, allows monitoring of a gas flow such as a respiratory or anesthetic gas. Online gas monitoring, however, requires an increased effort with respect to stabilizing the laser system.

If there are no changes of the applied active and passive components of the laser system, e.g. laser system 10 or 80, and as long as the environmental conditions remain unchanged, the light beam 60 (in the laser cavity 20 of FIG. 1A or in the external cavity 90 in FIG. 1B) will substantially remain at constant power. The light beam 60 circulating in the laser cavity 20 and the external cavity 90 comprises one or more (longitudinal) optical modes determined by the components of the laser system and the specific environmental circumstances within the respective cavity/cavities. Associated with each optical mode are a defined wavelength and a defined roundtrip phase shift. The gain medium 50 supports the optical mode(s) that match(es) the required wavelengths and provides the necessary phase, thus leading to a high intensity build-up light beam 60 at the supported optical mode(s).

It is to be understood that semiconductor type lasers generally only support one optical mode at a time, while other laser types (e.g. gas laser) may support more than one optical mode concurrently. For the sake of simplicity, only semiconductor type lasers, supporting only one optical mode at a time, shall be considered in the following. However, it is clear that the principals as illustrated herein are applicable for multi-mode concurrently supporting lasers accordingly.

In the coupled cavity system of FIG. 1B, a locking mechanism between the two resonators has to take place. To achieve substantial amplification and stability in the external cavity, the feedback of the external cavity into the laser cavity has to be adjusted, so that the laser diode radiation emits coherent radiation with a bandwidth and a wavelength to actively support the external cavity 90 at a cavity resonant frequency. This process is called hereinafter "optical locking".

When a change of the applied active and passive components (e.g. of the optical path length) of the laser system occurs and/or the environmental conditions change, the currently supported optical mode does not match anymore the required wavelength and phase shift, and the laser system has to 'find' another optical mode matching the changed resonating conditions within the laser system. Thus, the light beam 60 can suddenly extinguish (albeit temporarily) until a new optical mode is built up fitting to the changed cavity properties. This leads to a (significant and in most cases unwanted) variation of the optical power of the optical beam 60 over the time.

Figure 2:
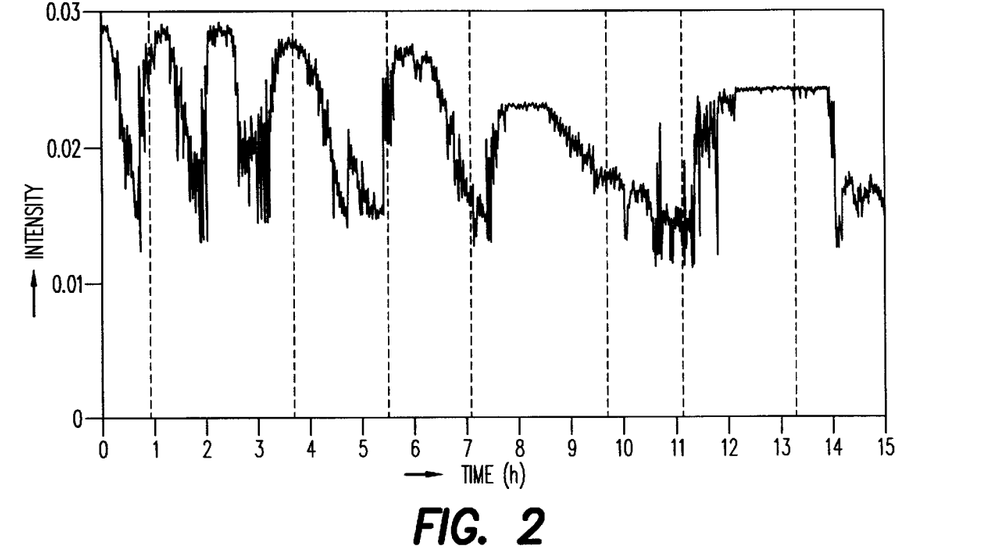
FIG. 2 shows an example of a variation of the optical power over the time in the external cavity 90 in an arrangement according to FIG. 1B, FIGS. 3A–3C depict a first embodiment of the invention and corresponding measuring results.

FIG. 2 shows an example of a variation of the optical power over the time in the external cavity 90 in an arrangement according to FIG. 1B. The power variations in the measurement example of FIG. 2 were possibly induced by temperature or other environmental variations causing modifications in the optical lengths of the laser system 80. When applied for Raman scattering, the power variation leads to different results for the Raman scattering measurement due to a variation in the exciting power.

A known possibility for avoiding environmental disturbances is disclosed in U.S. Pat. No. 5,245,405 for the gas analyzing cell as discussed above. A pressure control system eliminates pressure variations in the gas cell regardless of changes in restriction, gas viscosity and barometric pressure. Maintaining a constant pressure in the gas cell makes the system more stabile, since optical alignment through the gas cell is sensitive to gas pressure. Other known solutions suggest to arrange mechanical pumps for providing the gas flow as far as possible away from the gas analyzing cell in order to reduce disturbances by the pump as much as possible. However, although all of those solutions refer to gas analyzing purposes, they have been proved unpractical in several cases since the gas flow, in particular for respiration gases, is hardly controllable and always provides a source of disturbances, e.g. due to variations in the gas compounds.

A solution for an actively locked external optical resonator 90 is an external servo control loop, which changes the characteristics of the laser cavity 20 in a way that this cavity 20 remains locked to a single external cavity mode with a constant optical power. Parameters to change the characteristics of the laser cavity 20 are current and temperature of the active laser medium 50 as well as mechanical changes of the laser cavity 20. This solution, however, requires highly sophisticated countermeasures to ensure stabile conditions, and because of the necessary resolution, such a servo control loop can become very expensive and costly.

SUMMARY OF THE INVENTION

It is an object of the present invention to provide a laser system that is less sensitive for variations of the optical components and/or for environmental disturbances. The object is solved by the independent claims. Preferred embodiments are shown by the dependent claims.

According to the invention, the laser system is actively forced to jump between different optical modes, or, in other words, the laser system comprises means for providing a plurality of different optical modes. In contrast to conventional laser systems wherein different optical modes randomly (i.e. passively) occur, the inventive laser system actively provides the plurality of different optical modes and thus forces the laser beam to (preferably continuously) jump between the provided optical modes.

As long as the applied active and passive components of the laser system and/or the environmental conditions remain unchanged, the average optical power of the laser beam 60 in the inventive laser system, forcing the laser beam to jump between different optical modes, is decreased with respect to the substantially constant (equilibrium state) optical power of the single optical mode laser beam 60 in the conventional laser system. However, when the applied active and passive components of the laser system and/or the environmental conditions change, the optical power of the laser beam 60 in the conventional laser system will suddenly dramatically decrease until a new optical mode has been 'found' and built up, thus leading to significant power variations. Since the laser system according to the invention already provides a plurality of optical modes, the likelihood for the inventive laser system to 'find' a 'new' matching optical mode is significantly increased, so that the inventive laser system will generally 'recover' much faster from variations of the optical components and/or environmental disturbances. Moreover, since the average optical power of the unchanged inventive laser system is generally lower than the (equilibrium state) optical power of the unchanged conventional laser system, and thus the differences in optical power due to disturbances are smaller in the inventive laser system, the optical power in the inventive laser system can be significantly stabilized. Thus, forcing the laser system to jump between different optical modes preferably much more frequent than 'disturbances' of the laser system occur allows stabilizing the optical power in the resonator.

In most laser systems, the amplification of the laser beam 60 will be different for each optical mode. Therefore, the optical power might change from mode to mode. The optical power behavior of the laser beam 60 can be further stabilized by increasing the number of actively induced jumps between optical modes, in particular with respect to power averaging periods of the laser system. In case of Raman applications, e.g. for respiratory or anesthetic gas monitoring, the number of induced jumps between optical modes is preferably selected to be large during a time period wherein the Raman spectrum is averaged. Thus, the average optical power during that time period can be stabilized.

There are several ways to actively force the laser system to jump between different optical modes, such as varying the phase of the light beam or varying the optical length of the laser system. Other possibilities might be applied accordingly, however, varying phase and/or optical length have been proved to be the most practical.

Varying the phase of the laser, e.g. by adding phase to the light beam, can be achieved for example by varying (or dithering) the current and/or the temperature of a semiconductor laser as the gain medium 50, or by varying the refractive index, and thus the phase of the light, by means of electrical or mechanical forces. The temperature variation of the semiconductor laser is preferably performed with the semiconductor directly mounted to a cooling and/ or heating device. Phase changes of the semiconductor laser can thus be induced because the refractive index of the semiconductor laser is a strong function of the temperature.

Varying the optical length can be performed, for example, by varying (or dithering) the refractive index, e.g. by varying the cavity pressure or the physical cavity length(s), e.g. by moving one or more cavity mirrors or otherwise changing the mechanical length(s). The variation of the optical lengths in a coupled resonator system, as shown e.g. in FIG. 1B, can be executed in only one of the resonators and/or in all.

In particular for varying the optical length, 'natural' or inherent sources of disturbances in the applied laser system can be intentionally used for actively forcing the laser system to jump between different optical modes. For example, in a laser system wherein a pump pumps a gas to be monitored to the gas analysis cell 70, it can be made use of the inherent disturbances caused by the pumping for varying the cavity pressure. Whereas e.g. in U.S. Pat. No. 5,245,405 the pump is deliberately arranged as far as possible away from the gas analysis cell 70 in order to avoid disturbances, the invention suggests e.g. to intentionally arrange a pump close(r) to the gas analysis cell 70 in a way that the laser system is to actively forced to jump between different optical modes.

It is clear that in a multi-cavity laser system wherein the optical length of the system is determined by a plurality of individual optical lengths, varying the optical length of the system can be accomplished by varying one or more of the individual optical lengths. That means that e.g. in a coupled laser system as depicted in FIG. 1B, the optical length can be changed as well of the buildup cavity (external cavity 90) as of the laser cavity 20 (e.g. as the cavity between the back mirror of the diode laser and the input mirror of the buildup cavity), or even both. This can be done, for example, by changing the refractive index of the gas in either one or both cavities.

In strict contrast to conventional laser systems wherein the system is stabilized by (actively) carefully controlling the environment and restricting the bandwidth of the system to only one single mode, the laser system according to the invention is actively 'disturbed' so that the inventive laser system is forced to jump between optical modes and thus deliberately runs in a continuous multi-optical mode. This means that in case of (external) instabilities, the inventive laser system can jump to another stable mode to continue lasing, whereas in conventional laser systems lasing immediately will stop. Although the best performance (e.g. with respect to the achievable optical power in the cavity) of an optical laser system can be reached if only one single optical mode will be supported by the system, however, the inventive multi-optical-mode-system provides a higher overall stability, so that the requirements on environmental and mechanical stability as well as on optical filters can be reduced, with a significant impact on the price performance of the laser system e.g. for gas monitoring purposes.

It has to be noted that the principles of the invention also apply for laser systems concurrently supporting a plurality of optical modes (e.g. gas lasers). In that case, the laser system will be forced to concurrently jump between one or more different optical modes.

In a preferred embodiment, the numbers of optical modes supported by the inventive laser system is reduced to a discrete number of optical modes in order to restrict the bandwidth of the laser system. This can be achieved e.g. by providing respective wavelength filters like prism, grating and/or etalon. It has to be understood that the requirements of stability and bandwidth of the laser system are contradicting, so that a certain tradeoff has to be found for each application. In a specific embodiment employing Raman scattering, the provision of four optical modes (which can lase) has been found to provide a good and acceptable compromise between those requirements.

BRIEF DESCRIPTION OF THE DRAWINGS

Other objects and many of the attendant advantages of the present invention will be readily appreciated and become better understood by reference to the following detailed description when considering in connection with the accompanied drawings. Features that are or can be built up substantially equally or similarly are referred to with the same reference sign.

DETAILED DESCRIPTION OF THE INVENTION

Figure 3A:
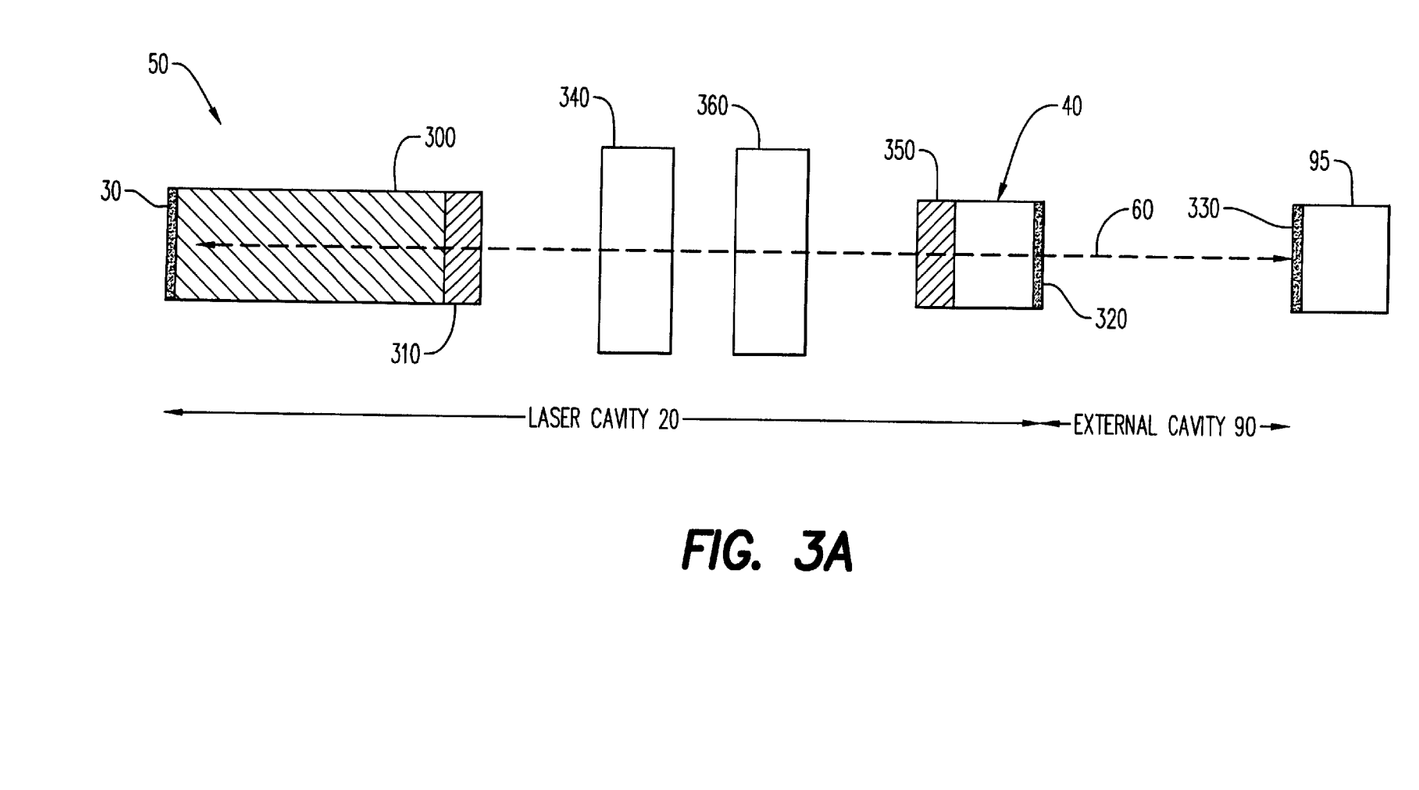

FIG. 3A shows a first embodiment of the invention wherein varying the phase of the laser can be achieved by varying the current and/or temperature of a semiconductor laser as the gain medium 50. The embodiment of FIG. 3A is based on the embodiment of FIG. 5 as disclosed in U.S. Pat. No. 5,642,375 by the same applicant and one of the present inventors. The shown embodiment employs a coupled laser system 80 as depicted in FIG. 1B, however, the laser system 10 according to FIG. 1A can be employed accordingly.

In FIG. 3A, the gain medium 50 is incorporated into the structure of a semiconductor diode laser 300. The back facet of the laser 300 is coated to be reflective and forms the surface 30. An emission facet 310 of the diode laser 300 is anti-reflection (AR) coated, with reflectivity preferably in the range of less than $10^{-3}$. Reflective surfaces 320 and 330 are coated onto the mirrors (substrates) 40 and 95, respectively. These surfaces have appropriate curvatures to support a stable spatial mode in the external cavity 90 (between the surfaces 320 and 330). Mode matching optics 340 (e.g. lenses and/or prisms) well known to those skilled in the art, can be used to spatially match the diode emission into the external cavity 90. A surface 350 of the mirror (substrate) 40 facing the laser cavity 20 is preferably anti-reflection coated with a reflectivity in the range about 0.04 to 0.001. Alternatively, the surface 350 can be a chamfer at an angle with the light path 60 to reduce its light reflection into the gain medium.

A frequency-limiting device 360 is preferably placed between the mode matching optics 340 and the mirror 40. In this way, the frequency-limiting device 360 produces the most effect using a minimum number of components. Such a system may be constructed using a Philips CQL 801D diode laser as the gain medium 50, having its emission facet 310 coated to have a reflectivity in the range of $10^{-5}$ to $10^{-4}$. The mode matching optics 340 preferably consists of an anti-reflection (AR) coated lens with a numerical aperture (NA) of 0.48 and focal length of 4.8 mm, an anamorphic prism pair (3:1), and a 25 cm focal length lens. The surfaces 320 and 330 may have a 17 cm radius of curvature, with reflectivities $R_{320}=0,999$ and $R_{330}=0,99999$. The length of the external cavity 90 may be 10 cm. Other details of the preferred embodiments can be obtained from U.S. Pat. No. 5,642,375.

The frequency-limiting device 360 in FIG. 3A is employed to filter out the undesirable frequencies in order to reduce the frequency bandwidth of the laser beam 60. The frequency-limiting devices 360 may include one or a combination of gratings, etalon, lyot filters, or dielectric stack filters. The rear surface of the diode laser gain medium 300 may be coated with a distributed Bragg reflector, which also limits the allowed frequencies in the laser system. Examples of applicable frequency-limiting devices 360 are described in great detail in U.S. Pat. No. 5,642,375.

Figure 3B:
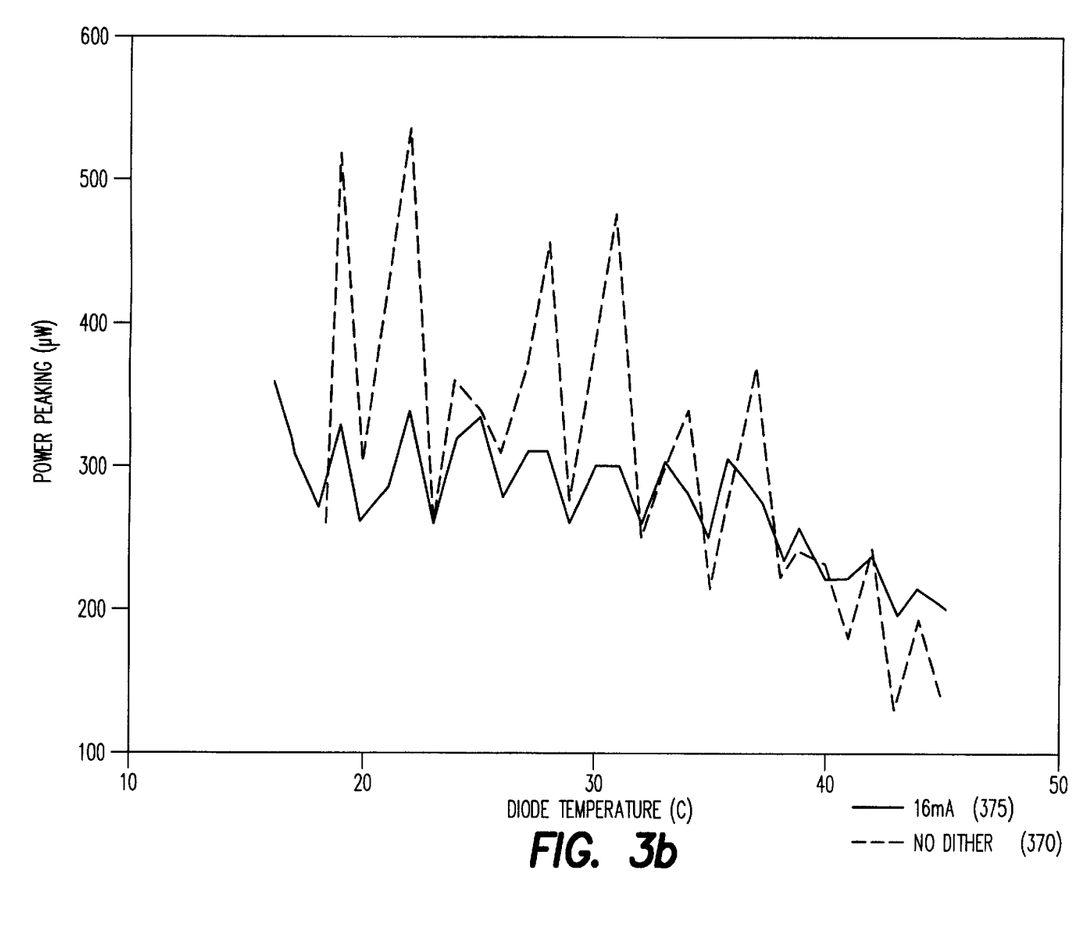
Figure 3C:
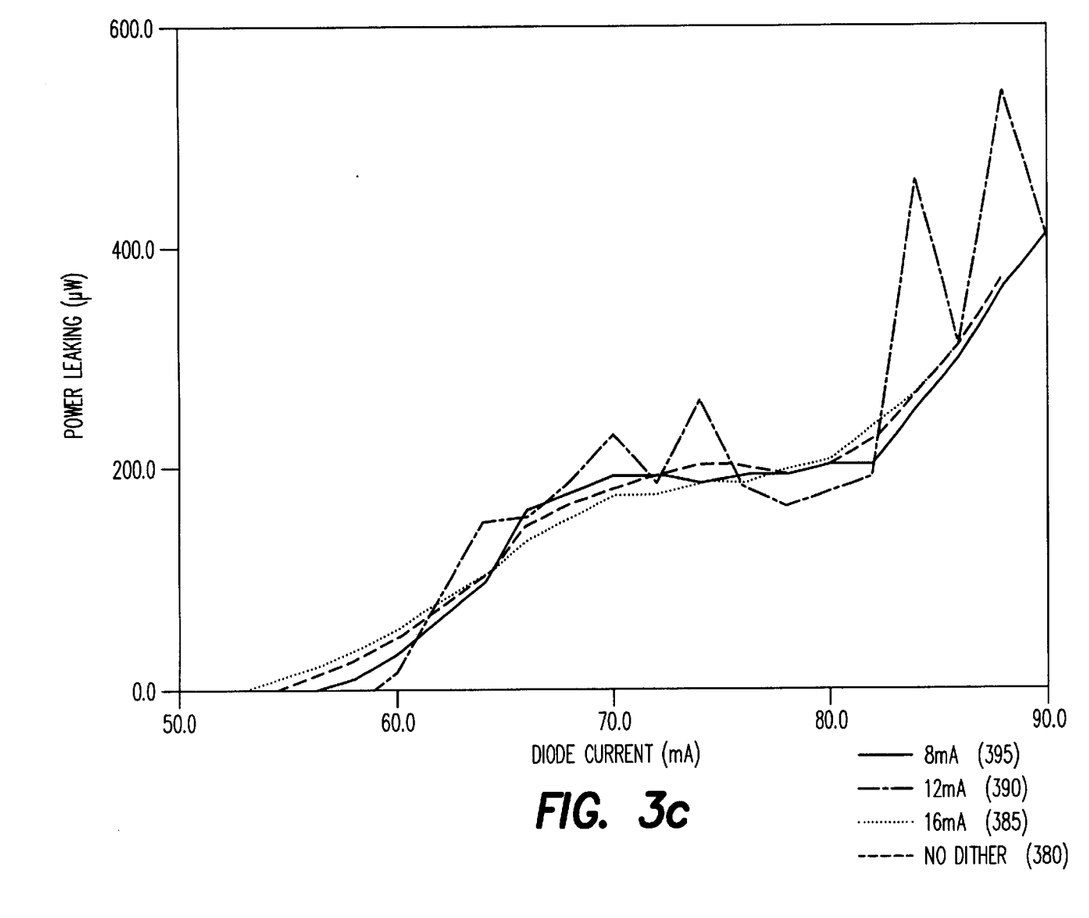

FIGS. 3B and 3C depict measuring results derived from an embodiment according to FIG. 3A. The average power that leaked out of the external cavity 90 is depicted on the Y-axis and was measured as a function (depicted on the X-axis) of the temperature (FIG. 3B) or the current (FIG. 3C) of the diode laser gain medium 300.

Dashed line 370 in FIG. 3B depicts the behavior of the power leakage versus diode temperature without dithering the current of the diode 300. Straight line 375, in contrast thereto, depicts a power versus temperature curve, whereby the current of the diode 300 has been dithered with a 100 Hz triangle wave with 16 mA peak-to-peak. Both lines 375 and 380 were measured for a current of the diode 300 of 86 mA.

FIG. 3C depicts power versus diode current behaviors. Dashed line 380 represents the power behavior when the diode current is not dithered. Lines 385, 390 and 395 display power behaviors, whereby the diode current has been dithered with 16 mA, 12 mA or 8 mA peak-to-peak, respectively.

The effect of the dithering becomes clear from FIGS. 3B and 3C. In both FIGS. 3B and 3C, without dithering the average power varied greatly with environmental changes (i.e. diode current and temperature). With dithering, the changes could be greatly smoothed out (particularly evident in FIG. 3B).

Figure 4A:
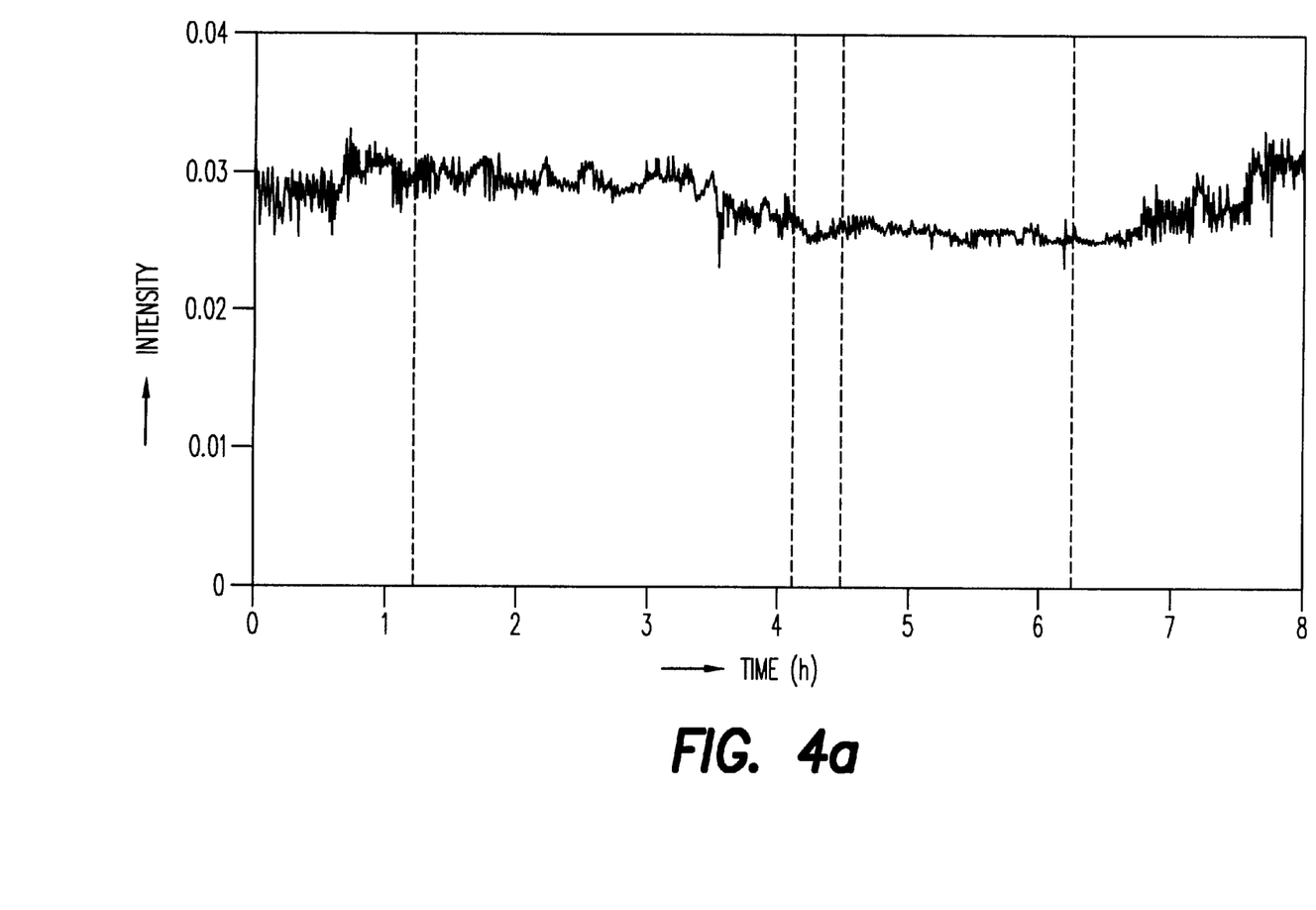
FIGS. 4A–4B depict the behavior of the optical power in the external resonator over the time and a long term measuring result in a laser system according to the invention.
Figure 4B:
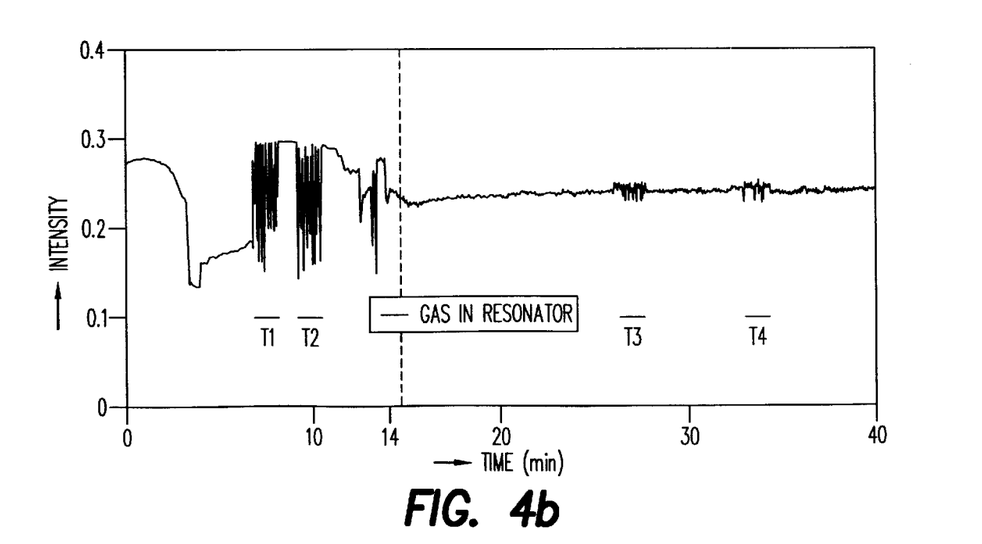

In another preferred embodiment, the optical length of the optical resonator (e.g. in a laser system according to FIG. A or 1B) is varied. FIGS. 4A and 4B display measuring results, wherein the refractive index of the laser cavity has been modified by varying the cavity pressure. It is to be understood that in case of coupled laser systems, a variation of the refractive index of each laser cavity will also vary the refractive index of the coupled laser system.

FIG. 4A shows the behavior of the optical power in the external resonator over the time in a laser system 80 according to FIG. 1B. In contrast to the measuring result as depicted in FIG. 2 for the same laser system, the refractive index of the optical resonator length has been varied by means of a 60 Hz air pressure pulsation within the external cavity 90. By comparing FIG. 4A with FIG. 2, it becomes apparent that the resonator intensity can be significantly stabilized by dithering the cavity pressure.

FIG. 4B depicts a long term measuring result for a laser system 80 according to FIG. 1B. The gas analysis cell 70 is provided for monitoring a respiration gas for medical purposes. All system parameters of the laser system 80 are maintained substantially constant except of the pressure within the gas analysis cell 70 which is maintained substantially constant during the first fourteen minutes and dithered with a frequency of approximately 60 Hz after fourteen minutes. During time periods T1, T2, T3 and T4, a respiration gas was directed through the gas analysis cell 70, thus leading to a significant variation of the resonator intensities during those periods of time. As apparent from FIG. 4B, the variation of the resonator intensity has been considerably stabilized after fourteen minutes by dithering the pressure within the external cavity 90. In particular during the periods of time wherein the respiration gas was directed through the gas analysis cells 70, the resonator intensity during the periods T3 and T4 has been dramatically stabilized with respect to the periods T1 and T2 without a dithering.

The embodiment corresponding to the FIGS. 4A and 4B might further comprise frequency-limiting devices 360 in order to limit the bandwidth of the laser beam 60. It is to be understood that the frequency limitation, either in FIG. 3A or in other embodiments according to FIGS. 1, is not necessary for the purpose of the invention to stabilize the optical power of the laser beam 60 against (environmental) disturbances, but only provides a useful parameter required for certain applications such as Raman scattering demanding a certain (frequency) bandwidth of the laser beam 60.

What is claimed is:

1. A laser system comprising:
   a gain medium for providing and amplifying a laser beam within an optical resonator;
   means for actively providing a plurality of different optical modes for stabilizing the laser beam; and
   means for actively inducing jumps between optical modes with frequencies greater than power averaging frequencies for monitoring an average power of the laser beam in the laser system, wherein the number of induced jumps between optical modes is increased during a time period wherein a Raman spectrum derived from the laser beam is averaged.

2. The laser system of claim 1, wherein the mode-providing means comprises means for forcing the laser beam to jump between different optical modes more frequently than environmental disturbances occur.

3. The laser system of claim 1, wherein the mode-providing means comprises means for forcing the laser beam to continuously jump between different optical modes.

4. The laser system of claim 1, wherein the mode-providing means comprises means for varying the phase of the laser beam.

5. The laser system of claim 4, wherein the means for varying the phase of the laser beam comprises means for varying a current of the gain medium.

6. The laser system of claim 4, wherein the means for varying the phase of the laser beam comprises means for varying a temperature of said gain medium.

7. The laser system of claim 4, wherein the means for varying the phase of the laser beam comprises means for varying a refractive index of said gain medium.

8. The laser system of claim 1, wherein the mode-providing means comprises means for varying the optical length of the optical resonator.

9. The laser system of claim 8, wherein the means for varying the optical length of the optical resonator comprises means for varying the refractive index of the optical resonator.

10. The laser system of claim 9, wherein said means for varying the refractive index of the optical resonator comprises means for varying a pressure of the optical resonator.

11. The laser system of claim 9, wherein said means for varying the refractive index of the optical resonator comprises means for varying a physical length of the optical resonator.

12. A method for stabilizing a laser beam in a laser system comprising a gain medium for providing and amplifying a laser beam within an optical resonator, said method comprising the steps of:
   actively providing a plurality of different optical modes for stabilizing the laser beam;
   actively inducing jumps between optical modes with frequencies greater than power averaging frequencies for monitoring an average power of the laser beam in the laser system; and
   increasing the number of induced jumps between optical modes during a time period wherein a Raman spectrum derived from the laser beam is averaged.

13. A gas monitoring system for monitoring a respiration and/or anaesthetic gas comprising:
   a laser system for providing a Raman spectrum of the gas to be monitored, further comprising:

a gain medium for providing and amplifying a laser beam within an optical resonator;

means for actively providing a plurality of different optical modes for stabilizing the laser beam; and means for actively inducing jumps between optical modes with frequencies greater than power averaging frequencies for monitoring an average power of the laser beam in the laser system, wherein the number of induced jumps between optical modes is increased during a time period wherein a Raman spectrum derived from the laser beam is averaged.

14. A laser system comprising:

a gain medium for providing and amplifying a laser beam within an optical resonator;

means for actively providing a plurality of different optical modes for stabilizing the laser beam; and a filter for reducing said plurality of different optical modes to a discrete number of optical modes to restrict the bandwidth of the laser system.

15. A laser system comprising:

a gain medium for providing and amplifying a laser beam within an optical resonator; and means for actively providing a plurality of different optical modes for stabilizing the laser beam further comprising means for varying the optical length of the optical resonator.

16. The laser system of claim 15, further comprising means for actively inducing jumps between optical modes with frequencies greater than power averaging frequencies for monitoring an average power of the laser beam in the laser system.

17. The laser system of claim 16, wherein the number of induced jumps between optical modes is increased during a time period wherein a Raman spectrum derived from the laser beam is averaged.

18. The laser system of claim 15, wherein the means for varying the optical length of the optical resonator comprises means for varying the refractive index of the optical resonator.

19. The laser system of claim 18, wherein said means for varying the refractive index of the optical resonator comprises means for varying a pressure of the optical resonator.

20. The laser system of claim 18, wherein said means for varying the refractive index of the optical resonator comprises means for varying a physical length of the optical resonator.

* * * * *